United States Patent [19]
Ito et al.

[11] Patent Number: 5,696,069
[45] Date of Patent: Dec. 9, 1997

[54] PERSONAL FOAMING CLEANSING COMPOSITION

[75] Inventors: Tsukasa Ito; David Story; Tomohiko Sano, all of Cincinnati, Ohio

[73] Assignee: The Andrew Jergens Company, Cincinnati, Ohio

[21] Appl. No.: 560,990

[22] Filed: Nov. 21, 1995

[51] Int. Cl.$^6$ .................. C11D 1/62; C11D 1/12; C11D 1/83

[52] U.S. Cl. .................. 510/123; 510/123; 510/124; 510/125; 510/127; 510/159; 510/494; 510/504; 510/505

[58] Field of Search .................. 510/123, 124, 510/125, 127, 159, 494, 504, 505

[56] References Cited

U.S. PATENT DOCUMENTS

| | | | |
|---|---|---|---|
| 4,111,827 | 9/1978 | Thompson et al. | 252/90 |
| 4,749,515 | 6/1988 | Miyamoto et al. | 252/545 |
| 5,017,305 | 5/1991 | Hoeffkes et al. | 252/311 |
| 5,116,543 | 5/1992 | Lentsch | 252/545 |
| 5,395,542 | 3/1995 | Nozaki et al. | 252/174.16 |
| 5,490,955 | 2/1996 | Hagan et al. | 252/554 |

*Primary Examiner*—Paul Lieberman
*Assistant Examiner*—Charles Boyer
*Attorney, Agent, or Firm*—Oblon, Spivak, McClelland, Maier & Neustadt, P.C.

[57] ABSTRACT

A detergent, personal cleansing or cosmetic composition comprising: a) one or more surfactants selected from anionic, nonionic, amphoteric, zwitterionic, and mixtures thereof, and which comprises at least one surfactant having a structure incorporating acyl taurate, b) quaternium cation, c) low HLB nonionic surfactants; and d) water, and wherein low HLB nonionic surfactants are in the form of a solution or dispersion.

10 Claims, No Drawings

PERSONAL FOAMING CLEANSING COMPOSITION

BACKGROUND OF THE INVENTION

1. Field of the Invention

The present invention relates to mild cleansing aqueous compositions in the form of solutions or dispersions and which comprise methyl taurate, cationic sufactants and low HLB nonionic surfactants. In particular, it relates to foam producing personal cleansing compositions suitable for simultaneously cleansing and conditioning the skin and/or the hair and which may be used, for example, in the form of foam bath preparations, shower products, skin cleansers, hand, face and body cleansers, shampoos, etc.

2. Background of the Prior Art

Foaming cosmetic and detergent compositions must satisfy a number of criteria including cleansing power, foaming properties and mildness/low irritancy with respect to the skin, hair and the ocular mucosae.

Ideal cosmetic cleansers should cleanse the skin or hair gently, without defatting and/or drying the hair and skin and without irritating the ocular mucosae or leaving skin taut after frequent use. Most lathering soaps, shower and bath products, shampoos and bars fail in this respect.

Certain synthetic surfactants are known to be mild. However, a major drawback of most mild synthetic surfactant systems when formulated for shampooing or personal cleansing is poor lather performance compared to the shampoos and bar soap standards. Thus, surfactants that are among the mildest, such as sodium lauryl glyceryl ether sulfonate, (AGS), provide marginal lather. The use of known high sudsing anionic surfactants with lather boosters, on the other hand, can yield acceptable lather volume and quality but at the expense of clinical skin mildness. These two facts make the surfactant selection, the lather and mildness benefit formulation process a delicate balancing act.

Despite the many years of research that have been expended by the toiletries industry on personal cleansing, the broad mass of consumers remain dissatisfied by the mildness of present day cleansing compositions, finding, for example, that they have to apply a separate cosmetic lotion or cream moisturizer to the skin after using a shower or bath preparation in order to maintain skin suppleness and skin hydration and also to counteract the delipidizing effect of cleanser.

Some products in the toiletries industry comprise high level of plant/animal/mineral oil in their formulation to maintain skin suppleness. However, due to high level of oil composition, the products lather marginally, and have an uncomfortable oily rinsing feeling. Oftentimes they are unstable under stressed temperature storage conditions.

Thus a need exists for personal cleansing products which will produce a foam which is abundant, stable and of high quality, which are effective hair and skin cleansers, which will not dehydrate the skin, which will provide a level of skin conditioning performance in a wash and rinse-off product which previously has only been provided by a separate post-cleansing cosmetic moisturizer, which has good viscosity characteristics and which at the same time has stable product and viscosity characteristics and remains fully stable under long term and stressed temperature storage conditions.

It has now been found that detergent, personal cleansing and cosmetic compositions having improved emolliency and product stability can be formed by the use of certain surfactant systems which comprises acyl taurate, cationic surfactants, and low HLB nonionic surfactants.

The present invention provides surfactant compositions comprising acyl taurate, cationic surfactants, and low HLB nonionic surfactants.

All concentrations and ratios herein are by active weight of the cleansing composition, unless otherwise specified; surfactant chain lengths are also on a weight average chain length basis, unless otherwise specified.

SUMMARY OF THE INVENTION

According to one aspect of the invention, there is provided a detergent, personal cleansing or cosmetic composition comprising: a) one or more surfactants selected from anionic, nonionic, amphoteric, zwitterionic, and mixtures thereof, and which comprises at least one surfactant having a structure incorporating acyl taurate, b) cationic surfactants, c) low HLB nonionic surfactants; and d) water, and wherein the low HLB nonionic surfactants are in the form of a solution or dispersion.

Another aspect of this invention is to provide a novel aqueous based cleansing and moisturizing product characterized by its mildness, long lasting softness, good lathering properties and acceptable stability under stressed temperature storage conditions.

DESCRIPTION OF THE PREFERRED EMBODIMENTS

In a highly preferred embodiment, the invention takes the form of a foam producing cleansing product suitable for personal cleansing of the skin or hair and which may be used as foam bath and shower products, skin cleansers and shampoos, etc.

According to this aspect, the invention relates to a foam-producing cleansing composition with superior lathering characteristics (creaminess, abundance, stability) combined with excellent mildness to the skin and hair, together with good stability, cleansing ability and conditioning performance. The invention also relates to a wash and rinse-off personal cleansing product having the above lathering, mildness, rinsibility, stability and conditioning benefit. The compositions of the invention comprise as an essential ingredient a surfactant having a structure incorporating acyl taurate, such a surfactant being referred to herein as taurate. The level of taurate is generally from about 0.1% to about 30% preferably from about 1% to about 15%, and more preferably from about 2% to about 7% by weight of composition. Taurates suitable for use in the compositions of the invention include:

RCONR'CH$_2$CH$_2$SO$_3$M wherein R is a C$_{8-20}$alkyl, preferably a C$_{12-15}$alkyl, R' is a C$_{1-4}$alkyl, and M is alkali metal, alkaline earth metal, ammonium or alkanolammonium. Commercial taurates are available, for example, sodium methyl cocoyl taurate (TAURANOL WS conc. (30%) available from Fintex, North Carolina, USA), sodium methyl oleoyl taurate (TAURANOL MS (32%) available from Fintex). These commercial preparations are supplied as pastes, powder, liquid, and flake form (e.g., Taurate Flakes, Rhone-Poulenc), Taurates may be produced by any of the following reactions:

1. dehydrochlorination of an acylchloride and a methyltaurine salt in the presence of an alkali,
2. dehydration of a fatty acid and an N-methyltaurine salt; or 3. deacetylation of isopropenyl fatty acid esters and an N-methyltaurine salt.

(see for example Miyazawa and Tamura, Cosmetics & Toiletries, vol. 108 March '93). Other conventional surfactants can also be present as co-surfactants. The relative amounts of taurates to co-surfactants will range in the weight ratio of about 1:4 to about 1:20, preferably from about 1:5 to about 1:10.

Example of suitable anionic co-surfactants include alkyl ether sulfates, alkyl ether carboxylates, alkyl ether sulfonates, sarcosinates, sulfosuccinates, alkyl amide ether carboxylates, potassium alkyl phosphate, alkyl amide methyl sulfate, carboxy ethyl glycine, alkyl-β-alanine an combinations of thereof. Alkyl ether sulfates useful in accordance with the present invention include those of the formula $$R(OCH_2CH_2)_nOSO_3M$$

wherein R ranges from $C_{8-20}$alkyl, preferably $C_{12-15}$alkyl, n is an integer from 1 to 20 preferably from 2 to 7, optimally from 2 to 3, and M is alkali metal, alkaline earth metal ammonium or alkanolammonium.

Alkyl ether carboxylates useful in accordance with the present invention include those of the formula $$R(OCH_2CH_2)_nOCH_2CO_2M$$

wherein R ranges from $C_{8-20}$ alkyl, preferably $C_{12-15}$ alkyl, n is an integer from 1 to 20, preferably from 2 to 7, optimally from 2 to 3, and M is alkali metal, alkaline earth metal, ammonium or alkanolammonium.

Alkyl ether sulfonates useful in accordance with the present invention include those of the formula $$R(OCH_2CH_2)_nSO_3M$$

wherein R ranges from $C_{8-20}$ alkyl, preferably $C_{12-15}$ alkyl, n is an integer from I to 20, preferably from 2 to 7, optimally from 2 to 3, and M is alkali metal, alkaline earth metal, ammonium or alkanolammonium.

Suitable sarcosinates useful in accordance with the present invention include accordance with the present invention include those of the formula $$RCON(CH_3)_nCH_2CO_2M$$

wherein R ranges from $C_{8-20}$ alkyl, preferably $C_{12-15}$ alkyl, n is an integer from 1 to 20, preferably from 2 to 7, optimally from 2 to 4, and M is alkali metal, alkaline earth metal, ammonium or alkanolammonium.

Alkyl amide ether carboxylates useful in accordance with the present invention include those of the formula $$RCONH(OCH_2CH_2)_nCH_2CO_2M$$

wherein R ranges from $C_{8-20}$ alkyl, preferably $C_{12-15}$ alkyl, n is an integer from 1 to 20, preferably from 2 to 7, optimally from 2 to 4, and M is alkali metal, alkaline earth metal ammonium or alkanolammonium.

Potassium alkyl phosphates useful in accordance with the present invention include those of the formula

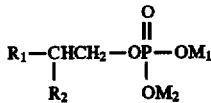

wherein $R_1$ ranges from $C_{8-20}$ alkyl, $R_2$ ranges from $C_{1-4}$ alkyl or hydrogen atom, $M_1$, and $M_2$ are independently, a potassium atom or a hydrogen atom.

Alkyl amide methyl sulfates useful in accordance with the present invention include those of the formula $$RNHCOCH_2OSO_3M$$

wherein R ranges from $C_{8-20}$ alkyl, preferably $C_{12-15}$ alkyl and M is alkali metal, alkaline earth metal, ammonium or alkanolammonium.

Carboxyethyl glycines useful in accordance with the present invention include those of the formula

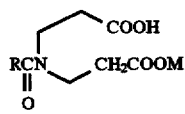

wherein R ranges from $C_{8-20}$ alkyl, preferably $C_{12-15}$ alkyl and M is alkali metal, alkaline earth metal, ammonium or alkanolammonium.

Alkyl-β-alanine useful in accordance with the present invention include those of the formula $$RCONHCH_2CH_2COOM$$

wherein R ranges from $C_{8-20}$ alkyl, preferably $C_{12-15}$ alkyl and M is alkali metal, ammonium or alkanolammonium.

Suitable nonionic surfactants include Triethylene glycol dodecyl ether Laureth-3, Oleth-3, Triethylene glycol tridecyl ether Trideceth-3, PEG-3 C9–11 acohol ether C9–11 Pareth-3, PEG-6 C9–11 alcohol ether C9–11 Pareth-6 as well as Triethylene glycol oleyl ether PEG20 Sorbitan Isostearate, PEG18 Glyceryl Oleate/Cocoate, Sorbitan Oleate.

Suitable amphoteric co-surfactants may include alkylbetaines, amidopropyl betaines, amido propyl sultaines, cocoamphoacetates, and combinations thereof.

Suitable alkylbetaines useful in accordance with the present invention include those of the formula $$RN(CH_3)_2CH_2CO_2M$$

wherein R ranges from $C_{8-20}$ alkyl, preferably $C_{12-15}$ alkyl, and M is alkali metal, alkaline earth metal, ammonium or alkanolammonium.

Suitable amidopropylbetaines useful in accordance with the present invention include accordance with the present invention include those of the formula $$RCONH(CH_2)_3N(CH_3)_2CH_2CO_2M$$

wherein R ranges from $C_{8-20}$ alkyl, preferably $C_{12-15}$ alkyl, and M is alkali metal, alkaline earth metal, ammonium or alkanolammonium.

Suitable alkylsultaines useful in accordance with the present invention include accordance with the present invention include those of the formula $$RNH(CH_2)_3N(CH_3)_2CH_2CO_2M$$

wherein R ranges from $C_{8-20}$ alkyl, preferably $C_{12-15}$ alkyl, and M is alkali metal, alkaline earth metal, ammonium or alkanolammonium.

Emollients are included to provide skin conditioning benefits and to improve the mildness of the products. The selection of the levels and types of moisturizers to be incorporated into the product is done in such a manner as not to adversely affect the stability of the product or its in-use characteristics, and still deliver good moisturization and lather.

The term "emollient" in this invention is used synonymously with the term moisturizer and is then meant to describe a material which imparts a smooth and soft feeling to the skin surface.

Also as used herein, "emollients" refer to materials used for the prevention or relief of dryness, as well as for the protection of the skin.

One way of reducing water loss from the stratum corneum is to deposit on the surface of the skin a layer which reduce the rate of evaporation. Another method is to add hygroscopic substances which will retain water, to the stratum corneum, to make this water available to the stratum corneum.

The emollients useful in the present invention are used in amounts of about 0.5% to 30%, preferably 1% to 15% by weight of the mild cleansing composition.

Known emollients such as hydrocarbon oils, wax, silicone oils, and triglycerides are regarded as good emollients. However, these emollients tend to suppress foam amount when used in high level. In this invention, cationic surfactants and low HLB nonionic surfactants are used to maintain high amounts of lather as well as to obtain good skin conditioning effect.

The compositions of the invention comprise as an essential ingredient, a cationic surfactant. The level of cationic surfactant is generally from about 0.05% to about 10% preferably from about 0.1% to 5% and optimally from about 0.1% to 1%. Cationic surfactants useful in accordance with the present invention include those of the general formula:

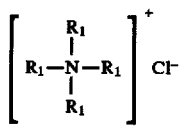

wherein $R_1$ is a $C_{1-20}$ alkyl, alkenyl or alkyl ester.

Commercial quaternium cationic surfactants are available, for example, distearyl dimonium chloride (Varisoft TA100, (99%) available from Witco, Greenwich Conn.), Quaternium 18 (Varisoft 442 100P, (99%) available from Witco), tricetylmonium chloride (Varisoft TC90, (95%) available from Witco). These commercial preparations are supplied as powder, paste, granule and liquid.

The compositions of the invention comprise as an essential ingredient low HLB nonionic surfactants. The level of total low HLB nonionic surfactants generally range from about 0.5% to about 20% preferably from about 1% to 15% and optimally from about 2% to 10%.

Low HLB nonionic surfactants useful in accordance with the present invention may include sorbitan esters having formulas:

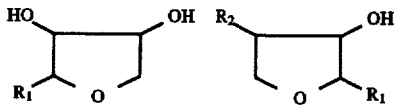

$R_1$: mono or diester of $C_{8-18}$ branched or straight-chain saturated, unsaturated, fatty acid $R_2$: mono ester of $C_{8-18}$ branched or straight-chain saturated, unsaturated fatty acid.

Commercial sorbitan esters are available, for example, sorbitan monooleate (Crill4, (99.5%) available from Croda, N.J., USA), sorbitan trioleate (Span85, (100%) available from ICI, Delaware, USA), sorbitan monoisostearate (Crill6,(99.5%) available from Croda, N.J., USA). These commercial preparations are supplied as solid and liquid.

Another low HLB nonionic surfactants useful in accordance with the present invention may include ethoxylated sorbitan esters having 1–80 moles of ethylene oxides in the above-mentioned sorbitan ester structure.

Commercial ethoxylated sorbitan esters are available, for example, Polysorbate 60(Crillet 3, (99.5%) available from Croda, N.J., USA), Polysorbate 80(Crillet 4,(100%) available from Croda), Polysorbate 120 (Crillet6,(99.5%) available from Croda). These commercial preparations are supplied as solid and liquid.

Another example of low HLB nonionic surfactants useful in accordance with the present invention may include ethoxylated vegetable oils and ethoxylated glyceryl esters.

Commercial ethoxylated vegetable oils are available, for example, PEG75 soybean glycerides, PEG20 soybean glycerides, PEG5 soybean glycerides, PEG75 palm kernel glycerides, PEG20 palm kernel glycerides, PEG5 palm kernel glycerides, PEG75 coconut oil glycerides, PEG20 coconut oil glycerides, PEG5 coconut oil glycerides (Acconon series, available from Abitec, N.J., USA), PEG18 glyceryl oleate/cocate (Antil 171,(85%) available from Goldshmit), PEG7 glyceryl cocoate (CetiolHE, available from Henkel), PEG12 glyceryl dioleate (Marlowet G 12 DO. Hüls America), PEG15 glyceryl oleate (Nikko TMGO-15, available from Nikko). These commercial preparations are supplied as paste and liquid.

As other optional ingredients, emulsifiers, humectants, thickening agents (such as hydroxypropyl methylcellulose, ethyl cellulose, magnesium aluminum silicate), preservatives, antioxidants (such as BHT), antibacterial agents (such as triclosan, benzalkonium chloride, benzethonium chloride, triclosan, triclocarban) and other conventional cosmetic additives may be present in the mild cleansing composition of the present invention.

Specifically, these additional additives will be incorporated in limited weight amounts selected so as not to interfere with the viscosity, "feel" and rinse-off characteristics of the cleansing composition. Such additives are conventional to those of skill in the art.

The viscosity of the final composition (Brookfield Model DV-I, spindle 4, 30 rpm, 25° C.) is preferably at least about 1,000 cps, more preferably from about 2,000 to about 30,000 cps, especially from about 5,000 to about 20,000 cps. Water is present at a level preferably of from about 30% to about 99%, more preferably at least about 60% by weight in the case of liquid compositions, and from about 5% to about 30% in the case of solid bar form compositions. The pH of the compositions is preferably from about 4 to about 9, more preferably from about 6 to about 8.

A preferred method for making the compositions herein comprises:

(a) disperse thickener, polymers comprising from about 0.1% to about 10% by weight of final composition in water phase;

(b) disperse or solubilize oil and nonionic surfactants comprising from about 1% to about 30% by weight of final composition to the (a) phase;

(c) mix auxiliary surfactant comprising from about 1% to about 30% by weight of final composition to (b) phase.

(d) mix methyl taurate comprising from about 1% to about 20% by weight of final composition to phase (c);

(e) add fragrance, and preservative to phase (d).

The invention is illustrated by the following non-limiting examples. In the examples, all concentrations are on an active weight % basis. The following methods were applied to evaluate the performance of each liquid detergent composition.

Lather performance:

A twenty-fold diluted aqueous solution of each of the liquid detergent compositions was provided for the test.

Foam volume was measured by Ross-Miles method at 25° C. Foam volume measured at 30 sec and 3 minutes after dropping solution to show the lather performance of flash and durability. The following symbols were given for each evaluation.

A: 400 ml or more (good)
B: 375–400 ml (fair)
C: less than 375 ml (poor)

Skin feel performance:

A panel consisting 5 people washed their hands with each composition under the conditions of 35° C. tap water and sensually evaluated them according to the following criteria:

Criteria: soft skin feel
A: Very soft
Slightly soft
C: Not soft

TABLE 1

| | Comparative Examples | | | | Examples of the Invention | | | |
|---|---|---|---|---|---|---|---|---|
| Example No. | 1 | 2 | 3 | 4 | 5 | 6 | 7 | 8 |
| Sodium Laureth Sulfate | 5.0 | 5.0 | 10.0 | 10.0 | 10.9 | 9.3 | 10.6 | 12.1 |
| Sodium Methyl Cocoyl Taurate | 2.0 | 2.0 | 7.0 | 7.0 | 2.7 | 2.3 | 2.5 | 3.0 |
| N-Myristoyl Sarcosine | 4.0 | 4.0 | 0.0 | 4.0 | 1.5 | 0.0 | 0.0 | 1.7 |
| N-Lauroyl Sarcosine | 4.0 | 4.0 | 4.0 | 0.0 | 2.3 | 3.3 | 3.3 | 2.6 |
| Laureth-4 Carboxylic Acid | 4.0 | 4.0 | 5.0 | 4.0 | 4.1 | 3.4 | 3.4 | 4.5 |
| Cocamidopropyl Betaine | 2.0 | 2.0 | 2.0 | 1.0 | 2.2 | 1.9 | 1.9 | 2.5 |
| Sodium Cocoamphoacetate | 0.8 | 0.8 | 0.0 | 1.0 | 0.8 | 0.0 | 0.4 | 0.9 |
| Lauryl Hydroxy Sultaine | 0.7 | 0.7 | 1.0 | 0.0 | 0.7 | 0.0 | 0.0 | 0.8 |
| Cocamid MEA | 2.5 | 2.5 | 0.0 | 0.0 | 2.4 | 2.1 | 2.5 | 2.7 |
| Sorbitan Oleate | 0.0 | 0.0 | 0.0 | 0.0 | 2.3 | 2.5 | 2.0 | 2.5 |
| PEG20 Sorbitan Isostearate | 0.0 | 0.0 | 0.0 | 0.0 | 0.9 | 0.0 | 0.0 | 1.0 |
| PEG20 Palm Kernel Oil Glycerides | 0.0 | 0.0 | 0.0 | 0.0 | 0.0 | 0.0 | 0.6 | 0.0 |
| PEG18 Glyceryl Oleate/Cocoate | 0.0 | 0.0 | 0.0 | 0.0 | 0.6 | 0.5 | 0.0 | 0.7 |
| Ethoxylated Soybean Glycerides | 0.0 | 0.0 | 0.0 | 0.0 | 0.8 | 0.7 | 0.7 | 0.9 |
| Trideceth-3 | 0.0 | 0.0 | 0.0 | 0.0 | 0.1 | 0.0 | 0.1 | 0.1 |
| Distearyl Dimonium Chloride | 0.0 | 0.0 | 0.0 | 0.0 | 0.2 | 0.2 | 0.2 | 0.2 |
| Hydroxypropyl Methylcellulose | 0.2 | 0.2 | 0.0 | 0.0 | 0.2 | 0.3 | 0.4 | 0.2 |
| Avocado Oil | 10.0 | 5.0 | 8.0 | 7.0 | 0.8 | 0.1 | 0.1 | 0.9 |
| Magnesium Aluminum Silicate | 1.4 | 1.4 | 0.0 | 0.0 | 1.4 | 1.2 | 1.2 | 1.5 |
| DMDM Hydantoin | 0.3 | 0.3 | 0.3 | 0.3 | 0.2 | 0.2 | 0.2 | 0.2 |
| Perfume | 1.0 | 1.0 | 1.0 | 1.0 | 1.0 | 1.0 | 1.0 | 1.0 |
| Glycerine | 2.5 | 2.5 | 0.0 | 0.0 | 2.4 | 2.4 | 2.4 | 2.4 |
| NaOH | 1.6 | 1.6 | 1.2 | 1.1 | 1.1 | 0.9 | 0.8 | 1.2 |
| Titinium Dioxide | 0.1 | 0.1 | 0.1 | 0.1 | 0.1 | 0.1 | 0.1 | 0.1 |
| Water | | | Balance to 100% | | | | | |
| Lather Performance/Ross-Miles Method Flash Lather (30 sec. after dropping) | C | A | C | C | B | A | B | A |
| Durable Lather (3 min. after) | C | A | C | C | B | A | B | A |
| Wash Sensory Evaluation | B | C | B | B | A | A | B | A |
| Note: | 1) | 2) | | | | | | |

1), 2), Separation at room temperature.

TABLE 2

| | Example No. | | | | | | | | | |
|---|---|---|---|---|---|---|---|---|---|---|
| | 9 | 10 | 11 | 12 | 13 | 14 | 15 | 16 | 17 | 18 |
| Sodium Laureth Sulfate | 5.0 | 5.0 | 5.0 | 5.0 | 5.0 | 5.0 | 5.0 | 5.0 | 5.0 | 5.0 |
| Sodium Methyl Cocoyl Taurate | 2.0 | 2.0 | 2.0 | 2.0 | 2.0 | 2.0 | 2.0 | 2.0 | 2.0 | 2.0 |
| N-Myristoyl Sarcosine | 4.0 | 0.0 | 4.0 | 8.0 | 0.0 | 4.0 | 0.0 | 4.0 | 8.0 | 0.0 |
| N-Lauroyl Sarcosine | 4.0 | 8.0 | 0.0 | 4.0 | 12.0 | 4.0 | 8.0 | 0.0 | 4.0 | 12.0 |
| Laureth-4 Carboxylic Acid | 4.0 | 4.0 | 8.0 | 0.0 | 0.0 | 4.0 | 4.0 | 8.0 | 0.0 | 0.0 |
| Cocamidopropyl Betaine | 2.0 | 2.0 | 2.0 | 2.0 | 2.0 | 2.0 | 0.7 | 2.0 | 2.0 | 0.7 |
| Sodium Cocoamphoacetate | 0.8 | 0.8 | 0.8 | 0.8 | 0.8 | 0.8 | 2.0 | 0.8 | 0.8 | 2.0 |
| Lauryl Hydroxy Sultaine | 0.7 | 0.7 | 0.7 | 0.7 | 0.7 | 0.7 | 0.8 | 0.7 | 0.7 | 0.8 |
| Cocamid MEA | 2.5 | 2.5 | 2.5 | 2.5 | 2.5 | 0.0 | 0.0 | 0.0 | 0.0 | 0.0 |
| Sorbitan Oleate | 2.0 | 0.0 | 0.0 | 0.0 | 2.0 | 2.5 | 2.9 | 3.0 | 2.5 | 2.9 |
| PEG20 Sorbitan Isostearate | 0.0 | 0.0 | 0.0 | 0.0 | 0.0 | 1.0 | 0.5 | 0.0 | 1.0 | 0.5 |
| PEG18 Glyceryl Oleate/Cocoate | 0.0 | 2.0 | 0.0 | 0.0 | 1.0 | 1.0 | 0.5 | 0.7 | 1.0 | 0.5 |
| Ethoxylated Soybean Glycerides | 0.0 | 0.0 | 2.0 | 2.0 | 0.0 | 5.4 | 6.0 | 6.2 | 5.4 | 6.0 |
| Trideceth-3 | 0.0 | 0.0 | 0.0 | 0.0 | 0.0 | 0.1 | 0.1 | 0.1 | 0.1 | 0.1 |
| Distearyl Dimonium Chloride | 0.1 | 0.1 | 0.1 | 0.1 | 0.1 | 0.2 | 0.2 | 0.2 | 0.2 | 0.2 |
| Hydroxypropyl Methylcellulose | 0.2 | 0.2 | 0.2 | 0.2 | 0.2 | 0.0 | 0.0 | 0.0 | 0.0 | 0.0 |
| Avocado Oil | 0.0 | 0.0 | 0.0 | 1.0 | 1.0 | 0.8 | 1.0 | 1.2 | 0.0 | 0.0 |
| Magnesium Aluminum Silicate | 1.4 | 1.4 | 1.4 | 1.4 | 1.4 | 0.0 | 0.0 | 0.0 | 0.0 | 0.0 |
| DMDM Hydantoin | 0.3 | 0.3 | 0.3 | 0.3 | 0.3 | 0.3 | 0.3 | 0.3 | 0.3 | 0.3 |
| Perfume | 1.0 | 1.0 | 1.0 | 1.0 | 1.0 | 1.0 | 1.0 | 1.0 | 1.0 | 1.0 |
| Glycerine | 2.5 | 2.5 | 2.5 | 2.5 | 2.5 | 2.5 | 2.5 | 2.5 | 2.5 | 2.5 |
| NaOH | 1.1 | 1.1 | 1.1 | 1.1 | 1.1 | 1.1 | 1.1 | 1.1 | 1.1 | 1.1 |
| Titinium Dioxide | 0.1 | 0.1 | 0.1 | 0.1 | 0.1 | 0.1 | 0.1 | 0.1 | 0.1 | 0.1 |
| Water | | | | Balance to 100% | | | | | | |
| Lather Performance/Ross-Miles Method Flash Lather (30 sec. after dropping) | B | — | — | — | A | — | — | — | — | B |
| Durable Lather (3 min. after) | B | — | — | — | A | — | — | — | — | B |
| Hand Wash Sensory Evaluation | A | — | — | — | A | — | — | — | — | B |

TABLE 3

| | \multicolumn{10}{c|}{Example No.} | | | | | | | | | |
|---|---|---|---|---|---|---|---|---|---|---|
| | 19 | 20 | 21 | 22 | 23 | 24 | 25 | 26 | 27 | 28 |
| Sodium Laureth Sulfate | 15.0 | 15.0 | 15.0 | 15.0 | 15.0 | 15.0 | 15.0 | 15.0 | 15.0 | 15.0 |
| Sodium Methyl Cocoyl Taurate | 7.0 | 7.0 | 7.0 | 7.0 | 7.0 | 7.0 | 7.0 | 7.0 | 7.0 | 7.0 |
| N-Myristoyl Sarcosine | 8.0 | 8.0 | 4.0 | 8.0 | 4.0 | 8.0 | 8.0 | 4.0 | 8.0 | 4.0 |
| N-Lauroyl Sarcosine | 8.0 | 4.0 | 8.0 | 4.0 | 4.0 | 8.0 | 4.0 | 8.0 | 4.0 | 4.0 |
| Laureth-4 Carboxylic Acid | 4.0 | 8.0 | 8.0 | 8.0 | 8.0 | 4.0 | 8.0 | 8.0 | 4.0 | 8.0 |
| Cocamidopropyl Betaine | 1.0 | 0.7 | 0.8 | 1.0 | 2.0 | 1.0 | 0.7 | 0.8 | 1.0 | 2.0 |
| Sodium Cocoamphoacetate | 0.8 | 1.0 | 0.7 | 3.0 | 1.0 | 0.8 | 1.0 | 0.7 | 3.0 | 1.0 |
| Lauryl Hydroxy Sultaine | 0.7 | 0.8 | 1.0 | 2.0 | 3.0 | 0.7 | 0.8 | 1.0 | 2.0 | 3.0 |
| Cocamid MEA | 0.0 | 0.0 | 0.0 | 0.0 | 0.0 | 0.0 | 0.0 | 0.0 | 0.0 | 0.0 |
| Sorbitan Oleate | 2.0 | 0.0 | 0.0 | 0.0 | 2.0 | 2.5 | 2.9 | 3.0 | 2.5 | 2.9 |
| PEG20 Sorbitan Isostearate | 0.0 | 0.0 | 0.0 | 0.0 | 0.0 | 1.0 | 0.5 | 0.0 | 1.0 | 0.5 |
| PEG18 Glyceryl Oleate/Cocoate | 0.0 | 2.0 | 0.0 | 0.0 | 1.0 | 1.0 | 0.5 | 0.7 | 1.0 | 0.5 |
| Ethoxylated Soybean Glycerides | 0.0 | 0.0 | 2.0 | 2.0 | 0.0 | 5.4 | 6.0 | 6.2 | 5.4 | 6.0 |
| Trideceth-3 | 0.0 | 0.0 | 0.0 | 0.0 | 0.0 | 0.1 | 0.1 | 0.1 | 0.1 | 0.1 |
| Distearyl Dimonium Chloride | 0.1 | 0.1 | 0.1 | 0.1 | 0.1 | 0.1 | 0.1 | 0.1 | 0.1 | 0.1 |
| Hydroxypropyl Methylcellulose | 0.0 | 0.0 | 0.0 | 0.0 | 0.0 | 0.0 | 0.0 | 0.0 | 0.0 | 0.0 |
| Avocado Oil | 0.0 | 0.0 | 0.0 | 1.0 | 1.0 | 0.0 | 0.0 | 0.0 | 0.0 | 0.0 |
| Magnesium Aluminum Silicate | 0.0 | 0.0 | 0.0 | 0.0 | 0.0 | 0.0 | 0.0 | 0.0 | 0.0 | 0.0 |
| DMDM Hydantoin | 0.3 | 0.3 | 0.3 | 0.3 | 0.3 | 0.3 | 0.3 | 0.3 | 0.3 | 0.3 |
| Perfume | 1.0 | 1.0 | 1.0 | 1.0 | 1.0 | 1.0 | 1.0 | 1.0 | 1.0 | 1.0 |
| Glycerine | 2.5 | 2.5 | 2.5 | 2.5 | 2.5 | 2.5 | 2.5 | 2.5 | 2.5 | 2.5 |
| NaOH | 1.8 | 1.8 | 1.8 | 1.8 | 1.8 | 1.8 | 1.8 | 1.8 | 1.8 | 1.8 |
| Titinium Dioxide | 0.1 | 0.1 | 0.1 | 0.1 | 0.1 | 0.1 | 0.1 | 0.1 | 0.1 | 0.1 |
| Water | \multicolumn{10}{c|}{Balance to 100%} | | | | | | | | | |
| Lather Performance/Ross-Miles Method Flash Lather (30 sec. after dropping) | B | — | — | — | B | — | — | — | — | A |
| Durable Lather (3 min. after) | B | — | — | — | B | — | — | — | — | A |
| Hand Wash Sensory Evaluation | A | — | — | — | A | — | — | — | — | A |

The mild, foaming cleansing composition of this invention has been described above by reference to specific example, as well as generic description. Alternatives within that generic description, employing different identities for those specifically enumerated, will occur to those of ordinary skill in the art without the exercise of inventive faculty. Such alternatives remain within the scope of the invention, safe for limitations expressly appearing in the claims below. In particular, other additives, proportions and the like may be altered, without the exercise of inventive skill.

What is claimed is:

1. A foam-producing personal cleansing composition, comprising:

a) a surfactant component, said surfactant component consisting essentially of, 1) a taurate of the formula

RCONR'CH$_2$CH$_2$SO$_3$M wherein R is a C$_{8-20}$alkyl, R' is a C$_{1-4}$alkyl, and M is alkali metal, alkaline earth metal, ammonium or alkanolammonium in an amount of from about 0.1 percent to about 30 percent by weight of the composition, 2) a cationic surfactant of the formula

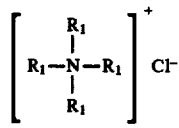

wherein R$_1$ is a C$_{1-20}$alkyl, alkenyl or alkyl ester in an amount of from about 0.05 percent to about 10 percent by weight of the composition, and 3) a solution or dispersion of a low HLB nonionic surfactant solution of compounds of the formula

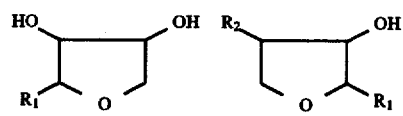

R$_1$: mono or diester of C$_{8-18}$ branched or straight-chain saturated, unsaturated, fatty acid and R$_2$: mono ester of C$_{8-18}$ branched or straight-chain saturated or unsaturated fatty acid, alkoxylated sorbitan esters of the above formula comprising 1–80 moles of ethylene oxides in the above sorbitan ester structure, alkoxylated vegetable oils and alkoxylated glycerol esters, said low HLB non-ionic surfactant being present in an mount of from about 0.5 percent to about 20 percent by weight of said composition, and b) water.

2. The composition of claim 1, wherein said surfactant component further consists essentially of other co-surfactants selected from the group consisting of alkyl ether sulfates, alkyl ether carboxylates, alkyl ether sulfonates, sarcosinates, alkyl amide ether carboxylates, alkyl amide methyl sulfates, carboxy ethyl glycine, alkyl-β-alanine, and combinations thereof.

3. The composition of claim 2, wherein said co-surfactants are present, with respect to the amount of taurate present, in a weight range of taurate to co-surfactant of about 1:4 to about 1:20.

4. The composition of claim 1, further comprising at least one compound drawn from the class consisting of humectants, thickening agents, preservatives, antioxidants, and antibacterial agents.

5. The composition of claim 1, wherein said taurate is present in an amount ranging from about 1 percent to about 15 percent by weight of the composition, said cationic surfactant is present in an amount ranging from about 0.1 percent to about 5 percent by weight of the composition and said low HLB nonionic surfactant is present in an amount ranging from about 1 percent to 15 percent by weight of said composition.

6. The composition of claim 5, wherein said taurate is present in an amount ranging from about 2 percent to about 7 percent by weight of the composition, said cationic surfactant is present in an amount ranging from about 0.1 percent to about 1 percent by weight of the composition and said low HLB nonionic surfactant is present in an amount ranging from about 2 percent to about 10 percent by weight of the composition.

7. A process for cleaning hair of an individual, comprising applying an effective amount of the composition of claim 1, to moistened hair, agitating said composition to form a lather, and rinsing said composition from said hair.

8. A method of cleansing skin of an individual, comprising moistening said skin, applying an effective amount of the composition of claim 1 to said skin, agitating said composition to produce a lather, and rinsing said composition from said skin.

9. The method of claim 7, wherein said hair is cleansed without substantial defatting or drying of said hair.

10. The method of claim 8, wherein said skin is cleansed without substantial defatting or drying of said skin.

* * * * *